| United States Patent [19] | [11] | 4,215,115 |
|---|---|---|
| DiSanzo | [45] | Jul. 29, 1980 |

[54] NEMATICIDAL PHOSPHORODITHIOATE

[75] Inventor: Carmine P. DiSanzo, Medina, N.Y.

[73] Assignee: FMC Corporation, Philadelphia, Pa.

[21] Appl. No.: 744,535

[22] Filed: Nov. 24, 1976

[51] Int. Cl.$^2$ .............................................. A01N 9/36
[52] U.S. Cl. .................................................... 424/216
[58] Field of Search ......................................... 424/216

[56] References Cited

U.S. PATENT DOCUMENTS

| 2,596,076 | 5/1952 | Hook et al. ....................... 424/216 X |
| 2,759,010 | 8/1956 | Lorenz et al. .................... 424/216 X |
| 3,474,170 | 10/1969 | Scharpf ................................. 424/285 |
| 3,651,225 | 3/1972 | Gordon ................................. 424/200 |
| 3,816,623 | 6/1974 | Griesbaum et al. ................. 424/215 |
| 3,878,267 | 4/1975 | Wagner, Jr. ......................... 260/948 |

*Primary Examiner*—Allen J. Robinson
*Attorney, Agent, or Firm*—Harrison H. Young, Jr.; H. Robinson Ertelt

[57] ABSTRACT

The compound O,O-diethyl S-(tert-butylthiomethyl) phosphorodithioate exhibits a broad spectrum of nematicidal activity.

1 Claim, No Drawings

NEMATICIDAL PHOSPHORODITHIOATE

This invention pertains to the general field of nematicides, particularly to agricultural nematicides used in the control of plant parasitic nematodes.

The active nematicidal compound of the present invention, O,O-diethyl S-(tert-butylthiomethyl) phosphorodithioate, is disclosed in U.S. Pat. No. 2,596,076 to have insecticidal activity. No reference has been found which discloses or suggests the nematicidal activity of the compound of the present invention.

This compound shows a broad spectrum of nematicidal activity when incorporated into the soil. Activity against the lesion nematode (*Pratylenchus penetrans*), against the stunt nematode (*Tylenchorhynchus claytoni*), and against the root-knot nematode (*Meloidogyne incognita*) has been demonstrated.

As noted above, O,O-diethyl S-(tert-butylthiomethyl) phosphorodithioate has been known for some time to possess insecticidal properties. A commercial sample of a 15% formulation on 25/50 mesh granules of attapulgite clay was obtained and was compared for nematicidal activity with a granular formulation of carbofuran, a commercial insecticide of chemical character vastly different from that of the phosphorodithioate, but which is known to have nematicidal properties (U.S. Pat. No. 3,474,170). To assure the authenticity of the commercial formulation used in testing, a sample was extracted and the ir spectrum of the extract compared with that of an authentic sample; the spectra were found identical. The nmr spectrum of the extract showed the four sets of peaks required of O,O-diethyl S-(tert-butylthiomethyl) phosphorodithioate:

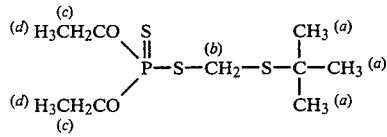

nmr δ (CDCl$_3$)
    a+d=1.4 (S+T, ~ 15H)
    b+c=4.2 (d+dofq, ~ 6H)
ir $\nu_{max.}^{liq.}$
    2962–2872 cm$^{-1}$ (CH$_3$ stretch)
    2926–2853 cm$^{-1}$ (CH$_2$ stretch)
    1390–1365 cm$^{-1}$ (t-butyl)
    1160 cm$^{-1}$ (P-OEt vibration)

EXAMPLE 1

Nematicidal Tests

A. Root-knot nematode (*Meloidogyne incognita*)

Tomato seedlings having two large true leaves were transplanted into six-inch clay pots containing steam-sterilized sandy soil. One week after transplanting, galled roots of nematode-infested tomato plants having fully developed egg masses of root-knot nematodes were inserted into the soil around the seedling roots. The plants were allowed to grow for 6–7 weeks after inoculation of the soil at which time fully developed egg masses were present.

The infested tomato roots were cleaned by rinsing thoroughly under running water, the clean roots were cut into short pieces, and comminuted with water in a blender for 30 seconds. The shredded roots were poured onto layers of washed sand contained in a standard greenhouse flat. The flat was covered with a thin plastic sheet and kept at greenhouse temperature until about 50% of the larvae had emerged (3–7 days). The sand containing larvae and eggs was mixed in a twin-shell blender for 30 seconds to obtain uniform distribution of the eggs and larvae.

The population of nematodes was estimated using the method of Caveness and Jensen (Proc. Helm. Soc. Washington 22, 87–89 (1955)). The infested sand was blended with sufficient steam-sterilized sandy soil to give a final mixture containing 600–800 nematode larvae and eggs per 300 grams of mixture.

The 15% granular formulation of O,O-diethyl S-(tert-butylthiomethyl) phosphorodithioate ("Compound A" in the tabulations below) or a 15% granular formulation of carbofuran was blended with samples of this infested mixture to give the desired concentration of active ingredient. Tomato seedlings having two large true leaves were transplanted into 3-inch pots containing the chemically-treated infested soil. The seedlings were allowed to grow for two weeks with normal watering, then the soil in which the seedlings were growing was allowed to dry until the plants began to wilt. The roots were shaken to remove the soil and the knotting compared to that on plants growing in the same infested soil which had received no chemical treatment. The activity is recorded as the percent decrease in knotting. Table 1 summarizes the results of the comparisons.

B. Stunt nematode (*Tylenchorhynchus claytoni*)

The stunt nematode was cultured on alfalfa callus tissue kept in an incubator at 21° C. The contents of the culture tube were suspended in a Baerman filter and the surface of the filter was subjected to intermittent mist spray for 24 hours during which the nematodes migrated through the filter and were collected in the receiving tube. The population of nematodes in the suspension was determined by counting, under a stereomicroscope, the number present in an aliquot (usually 0.10 to 0.50 ml) of the suspension.

The test tobacco plant (*Nicotiana tabacum* var. Turkish) growing in a 4-inch pot in soil treated as described in A above, was inoculated by depositing around the base of the plant sufficient volume of the aqueous suspension to provide 3000–4000 nematodes. Forty days after inoculation, the soil was processed to determine nematode population. The soil was thoroughly mixed and a 200-cubic-centimeter aliquot was taken for nematode analysis. The soil sample was placed in a 250-ml beaker and sufficient water was added to thoroughly soak the soil. After approximately 15 minutes, the contents of the beaker were poured onto a 20 mesh sieve and the soil washed under running tap water until about one gallon of wash water had been collected. The collected wash water was stirred for approximately 30 seconds, then washed through an 8-inch-diameter 325 mesh sieve. The material collected on the sieve was transferred into a 250-ml beaker and stirred with approximately two volumes of water. This mixture was poured through a 3-inch 325 mesh sieve and the material collected (approximately 60 ml) on the sieve returned to the beaker. The mixture was transferred into two 50-ml centrifuge tubes which were centrifuged at 420 G for five minutes. The supernatant, with light debris in suspension, was discarded and replaced by a sugar solution (454 grams sugar/liter) of specific gravity 1.18. The sediment was put into suspension by stirring and the tubes were centrifuged a second time for 30 seconds. The supernatant containing the nematodes was collected into a counting dish and counted under a stereomicroscope. The results are shown in Table 2.

C. Lesion nematode (*Pratylenchus penetrans*)

The lesion nematode was cultured as described in B above. The test pea plant (*Pisum sativum*, var. Hundredfold) growing in a 4-inch pot in soil treated as described in A above was inoculated as described in B above. Forty days after inoculation the soil was processed to determine the nematode population as described in B above.

In tests that involved the lesion nematode, the population was determined in the roots of the plants as well as in the soil. The root systems of the host plants were washed clean under running water and 3–5 grams of the fine feeder roots were collected. These roots were then placed in a modified Baerman funnel. The surface of the filter was subjected to intermittent mist spray at 21° C. for two weeks during which the nematodes migrated through the funnel and were collected in the receiving tube. Nematodes were concentrated in a small amount of water by transferring the contents of the receiving tube into a funnel which was closed at the stem by means of a rubber hose and a clamp. Air bubbles were removed from the funnel by depressing and releasing the rubber hose above the clamp several times. After a minimum of 3 hours the water in the funnel was stirred to put in suspension nematodes remaining on the wall of the funnel. After one additional hour, nematodes were drawn off the bottom of the funnel stem by slowly releasing the clamp. Approximately 10 ml of water was collected and put into a counting dish where the nematode population was counted using a stereomicroscope. The counting procedure was done twice at weekly intervals during the two-week period. The results are shown in Table 3.

Table 1

Nematicidal Activity Against Root-Knot Nematodes on Tomatoes

| Test Compound | | Percent Nematode Control at ppm of Compound | | | |
|---|---|---|---|---|---|
| | | 25 | 10 | 5 | 2.5 |
| Compound A | (a) | 100 | 100 | — | 77.5 |
| | (b) | 99 | 91.3 | 87.8 | 56.3 |
| Carbofuran | (a) | 81.3 | 76.3 | — | 56.3 |
| | (b) | 98 | 86.5 | 70 | 70 |

(a) and (b) were comparisons at separate times

Table 2

Nematicidal Activity Against the Stunt Nematode on Tobacco (40 days after treatment)

| Test Compound | Nematodes/Pot* at ppm of Compound | | | |
|---|---|---|---|---|
| | Incorporated | | Surface | |
| | 10 | 5 | 10 | 5 |
| Compound A | 432 | 588 | 546 | 738 |
| Carbofuran | 751 | 853 | 503 | 564 |
| None | ---------- 1801 ---------- | | | |

*Average of 5 replicates

Table 3

Nematicidal Activity Against the Lesion Nematode on Peas (40 days after treatment)

| Test Compound | Nematodes/Root System* at ppm of Compound | | | |
|---|---|---|---|---|
| | Incorporated | | Surface | |
| | 10 | 5 | 10 | 5 |
| Compound A | 48 | 92 | 10 | 50 |
| Carbofuran | 152 | 524 | 150 | 236 |
| None | ---------- 754 ---------- | | | |

*Average of 5 replicates

The active nematicidal compound of this invention may be formulated with any of the relatively inert adjuvants and carriers normally employed for facilitating the dispersion of active ingredients for agricultural applications, recognizing the fact that the formulation and mode of application of a toxicant may affect the activity of the material in a given application. If the formulation permits even distribution of the active ingredients and provides contact with the area to be treated, the precise nature of the formulation is not critical. Thus, O,O-diethyl S-(tert-butylthiomethyl) phosphorodithioate may be formulated as a granule, in wettable powders, in emulsifiable concentrates, in solution, or as any of several other known types of formulations depending on the desired mode of application. These formulations may contain as little as 0.5% to as much as 95% or more by weight of active ingredient.

In granular formulations, for example, the active compound is spread on the surface of, or absorbed into, a granular carrier of relatively coarse particles, which may be inert or may be a fertilizer or other active material. Typical carriers for granular formulations include sand, fuller's earth, bentonite clays, vermiculite, perlite and other organic or inorganic material. Granular formulations, usually applied without dilution to the area in which suppression of nematodes is desired, normally are prepared to contain about 5–25% active ingredient and agents or emulsifiers; oils such as heavy aromatic naphthas, kerosene or other petroleum fractions, or vegetable oils; and/or stickers such as dextrins, glue or synthetic resins. The average particle size of the granules is usually between 150 and 2400 microns. For example a useful granular formulation contains 5.05 parts by weight of the active material, 5.00 parts by weight of corn oil and 89.95 parts by weight of crushed corn cobs.

Wettable powders are in the form of finely divided particles which disperse readily in water or other dispersant. The wettable powder is ultimately applied either as a dry powder or as a suspension in water or other liquid. Typical carriers for wettable powders include fuller's earth, kaolin clays, silicas or other readily wet organic or inorganic diluents. Wettable powders normally are prepared to contain about 5 to 95% of active ingredient, depending on the absorbency of the carrier, and usually also contain a small amount of a wetting or dispersing agent. For example, a useful wettable powder formulation contains 25.0 parts of O,O-diethyl S-(tert-butylthiomethyl) phosphorodithioate, 72.0 parts of attapulgite clay, and 1.5 parts of sodium lignosulfonate and 1.5 parts of sodium alkylnaphthalenesulfonate as wetting agents.

Emulsifiable concentrates are homogeneous liquid or paste compositions which are dispersible in water or other dispersant, and may consist entirely of the phosphorodithioate with a liquid or solid emulsifying agent, or may also contain a liquid carrier, such as xylene, heavy aromatic naphthas, dimethyl sulfoxide, isophorone, and other nonvolatile organic solvents. For application, these concentrates are dispersed in water or other liquid carrier, and normally applied as a spray to the area to be treated. The percentage by weight of the essential active ingredient may vary according to the manner in which the composition is to be applied, but in general comprises 0.5 to 95% of the agricultural composition.

Other useful formulations for agricultural applications include simple solutions of the active compound in dispersant in which it is completely soluble at the desired concentration, such as acetone, alkylated naphthalenes, xylene, or other organic solvents.

Typical wetting, dispersing, or emulsifying agents used in agricultural formulations include, for example, the alkyl or alkylaryl sulfonates and sulfates and their sodium salts; polyethylene oxides; sulfonated oils; fatty-acid esters of polyhydric alcohols; and other types of surface-active agents, many of which are available in commerce. The surface-active agent, when used, normally comprises from 1 to 15% by weight of the composition.

These formulations may be applied without further dilution or as dilute solutions, emulsions or suspensions in water or other suitable diluent. The compositions may be applied to the area where treatment is desired by spraying in the case of liquid compositions, or by distribution from mechanical equipment in the case of solids.

The active nematicidal compound of this invention may be formulated or applied with insecticides, fungicides, herbicides, plant growth regulators, fertilizers and other agricultural chemicals. In applying the compound of this invention, whether alone or with other agricultural chemicals, an effective amount and concentration of the active phosphorodithioate are of course employed.

It is apparent that modifications may be made in the formulation and application of the compound of this invention, without departing from the novel concept as defined in the following claims.

I claim:

1. A method of combating nematodes which comprises applying to the locus where nematodes are to be controlled a nematicidally effective amount of O,O-diethyl S-(tert-butylthiomethyl) phosphorodithioate.

* * * * *

Disclaimer and Dedication 4,215,115.—*Carmine P. Disanzo*, Medina, N.Y. NEMATICIDAL PHOSPHORODITHIOATE. Patent dated July 29, 1980. Disclaimer and Dedication filed Dec. 3, 1980, by the assignee, *FMC Corporation*.

Hereby disclaims and dedicates to the Public claim 1 of said patent.

[*Official Gazette January 27, 1981.*]